United States Patent [19]

Klein et al.

[11] 4,385,813
[45] May 31, 1983

[54] PHOROPTER

[75] Inventors: Friedrich Klein, Wedel; Joachim Burmeister, Brombach; Nils Warming, Hamburg, all of Fed. Rep. of Germany

[73] Assignee: J. D. Möller Optische Werke GmbH, Wedel, Fed. Rep. of Germany

[21] Appl. No.: 368,698

[22] Filed: Apr. 15, 1982

Related U.S. Application Data

[63] Continuation of Ser. No. 98,039, Nov. 28, 1979, abandoned.

[30] Foreign Application Priority Data

Jan. 16, 1979 [DE] Fed. Rep. of Germany ....... 2901459

[51] Int. Cl.³ .......................... A61B 3/10; A61B 3/02
[52] U.S. Cl. .................................... 351/217; 351/235
[58] Field of Search ...................... 351/11, 12, 28, 29

[56] References Cited

U.S. PATENT DOCUMENTS 1,873,356  8/1932  Stimson et al. ........................ 351/29
4,185,896  1/1980  Buhler .................................... 351/29

FOREIGN PATENT DOCUMENTS 947359  1/1964  United Kingdom .................. 351/29

*Primary Examiner*—John K. Corbin
*Assistant Examiner*—Rodney B. Bovernick
*Attorney, Agent, or Firm*—Toren, McGeady and Stanger

[57] ABSTRACT

Method for obtaining cross cylinder-like actions for using the adjusting or aligning measurement known as the cross cylinder method in phoropters for subjective refraction, wherein the spherical and cylindrical lens discs of the phoropter are adjusted in preprogrammed manner to cross cylinder-like lens systems.

The set problem is also solved by a phoropter with spherical test lenses and cylindrical lenses arranged on lens discs and which can be introduced into the observation optical path, wherein the motor drives of the lens discs are combined in a program control unit, connected to an operating unit and an indicating unit.

9 Claims, 2 Drawing Figures

PHOROPTER

This is a continuation of application Ser. No. 098,039, filed Nov. 29, 1979 now abandoned.

BACKGROUND OF THE INVENTION

The invention relates to a method for obtaining cross cylinder-like actions for using the adjusting or aligning measurement known as the cross cylinder method in phoropters for subjective refraction and a phoropter for performing the method.

For the application of the adjusting or aligning measurement called the cross cylinder method, devices are known which, in a mechanically guided manner, either in free-handed manner as a stem cross cylinder or as additional components for the device, are pivoted in front of the observation aperture of a pair of test spectacles or a phoropter. These components, which can be constructed in various ways, generally contain one or more cross cylindrical lenses.

By means of such devices, it is possible to check whether the eye being tested requires an astigmatic correction and the value and the axial position of the necessary cylindrical lens can be determined by adjustment or alignment.

BRIEF SUMMARY OF THE INVENTION

The problem of the invention is to provide cross cylinder-like actions in the complete field of use of the cross cylinder method from the test lenses required in a phoropter for subjective refraction.

According to the invention, this problem is solved in that the spherical and cylindrical lens discs of the phoropter are adjusted in preprogrammed manner to cross cylinder-like lens systems.

The invention also relates to a method wherein, while excluding cross cylindrical optical bodies using the lenses necessary for representing the spherical and cylindrical correction of a visual error by the same-time, rapid modification of the spherical and cylindrical value, as well as the axial position of the cylindrical lenses, a corresponding optical action of a cross cylindrical lens, which is otherwise additionally connected upstream for cylinder alignment purposes is mathematically determined, programmed and motor-transmitted to the spherical and cylindrical lens discs of the phoropter.

Using the lenses employed for the spherical and cylindrical correction of the visual error by same-time rapid modification of the spherical and cylindrical value, as well as the axial position of the cylindrical lenses at the same time the mathematically determined and programmed optical action of a cross cylindrical lens otherwise additionally connected upstream for cylinder alignment purposes is adjusted in such a way that, for testing the astigmatism, the upstream-connected spherical lens can be replaced by a spherical lens with a more powerful dioptric action and can be combined with a cylindrical lens of double the action and negative sign of the amount of the spherical change and in coarsely graded angular positions can be connected into the observation optical path, while for the axial alignment of the cylindrical portion of the lens combination, it can be pivoted in both the positive and negative rotation direction by the same amount about a randomly set axial position and the direction preferred by the patent is reset or the initial value is reset and for cylinder power adjustment the introduced lens combination is modified additively or subtractively, while in the case of a change with the same axial position of the cylindrical lenses a spherocylindrical combination is obtained, whose cylindrical portion represents twice the value of the spherical change, but has the opposite sign.

The set problem is also solved by a phoropter with spherical test lenses and cylindrical lenses arranged on lens discs and which can be introduced into the observation optical path, wherein the motor drives of the lens discs are combined in a program control unit, connected to an operating unit and an indicating unit.

By means of the method according to the invention and the appropriately constructed phoropter, a cross cylinder-like action is obtained with the test lenses for visual correction in the phoropter, without it being necessary to use additional components or lenses. It is only necessary to use the lenses conventionally employed for visual correction purposes, the set dioptric value for the sphere and the cylinder with its axial position is rapidly changed and with the same time, which is possible due to the electrical drives and program control unit employed.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
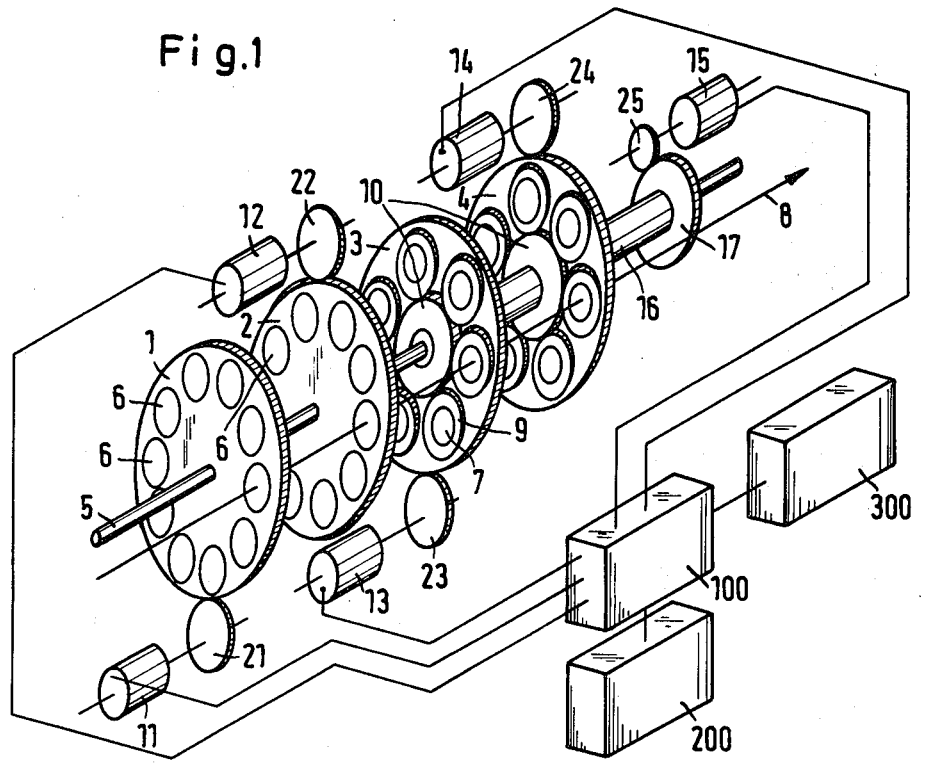
FIG. 1 the internal construction of a phoropter in a perspective view.

According to FIG. 1 the phoropter, whose casing is not shown, has a plurality of lens discs 1, 2, 3, 4, which are either arranged in axially parallel manner or are successively arranged in individually rotatable manner on a common shaft 5. These lens discs 1, 2, 3, 4 contain test lenses, distributed over the individual lens discs 1, 2, 3, 4 in such a way that the patient can be provided in the observation optical path 8 with a plurality of lens combinations in a continuous and uniform grading.

In the case of the embodiment shown in FIG. 1, the lens disc 1 carries spherical test lenses 6 in coarse grading, lens disc 2 spherical lenses in fine grading, lens disc 3 cylindrical lenses 7 in coarse grinding and lens disc 4 cylindrical lenses 7 in fine grading. The supports 9 for cylindrical lenses 7 are constructed as planet wheels in such a way that, besides the pivotal movement for changing the cylindrical lenses 7, driven by a sun wheel 10, they can also be jointly rotated about their own central axis for setting the axial position. By corresponding design of the planet gear, it is possible that once the axial position is set it can be retained despite the cylinder change. The sun wheels 10 are connected with one another and with a toothed gear 17, which engages with a pinion 25 by means of a second shaft, which is, for example, constructed as a hollow shaft 16. An electromotive drive 15 is used for the axial rotation of the cylindrical lenses 7.

In the same way lens discs 1, 2, 3, 4, which are constructed as toothed gears and engage in each case with a pinion 21, 22, 23, 24, are caused to rotate by their motor drives 11, 12, 13, 14 for the purpose of changing the lenses.

All the drives 11, 12, 13, 14 are controllable and logically interconnectable by means of a control unit 100. It is advantageous if stepping motors are used for the electrical drives 11, 12, 13, 14, because this permits a precise positioning of the individual lens discs 1, 2, 3, 4 without an actual value pickup, no matter whether in the form of potentiometers or absolutely coded sliders or light barriers. On the one hand, control unit 100 is connected to the indicating unit 300, which indicates in electrical form, for example, in digital numbers, the sphere, the cylinder and the axial position of the cylinder set in the phoropter and on the other hand is connected to an operating unit 200, making it possible for the person operating the phoropter to carry out these operations by means of control unit 100.

Cross cylinders are known. A cross cylinder is an astigmatic lens comprising two plane cylinders displaced by 90°, having the same refractive value, but opposite signs. A cross cylinder is also formed by the combination of a spherical lens with a positive action and a cylindrical lens with a negative action and double the refractive value. If, for example, the phoropter permits a grading for the sphere and the cylinder of, in each case, 0.25 dpt on changing the sphere by +0.25 dpt and the cylinder by −0.50 dpt, the cross cylinder can produce ±0.25 dpt. This combination of the change compared with the set values in the phoropter is fixed-programmed in the control unit 100 with the drives together with the appropriate instructions for performing the position change and by depressing the keys once can be read out via the operating unit.

When testing for astigmatism, the spherically precorrected eye is offered this change with various axial positions, for example 0°, 90°, 45° and 135° of the cylindrical lens.

A thus constructed phoropter is used in such a way that with the spherical test lenses 6 and the cylindrical lenses 7 for the spherical and cylindrical correction of the visual error of a patient by the same-time, rapid modification of the spherical and cylindrical value, as well as the axial position of the cylindrical lenses, it is also possible to simultaneously adjust the mathematically determined and programmed similar optical action of a cross cylindrical lens which is otherwise additionally connected upstream for cylinder alignment purposes in such a way that for testing the stigmatism the upstream-connected spherical test lens 6 can be replaced by a test lens 6 with a more powerful dioptric action. It can be combined with a cylindrical lens 7 of double the action and negative sign of the amount of the spherical change and can be connected in the observation optical path in coarsely graded angular positions. For axial alignment purposes, the cylindrical portion of the lens combination can be pivoted about the set axial position by the same amount in both the positive and negative rotation direction and the direction preferred by the patient can be reset or there can be resetting to the initial value. For cylinder power alignment purposes, the introduced lens combination can be additively or subtractively changed, whereby the change with the same axial position of the cylindrical lenses 7 once again represents a spherocylindrical combination, whose cylindrical portion represents double the value of the spherical change, but is of opposite sign.

Figure 2:
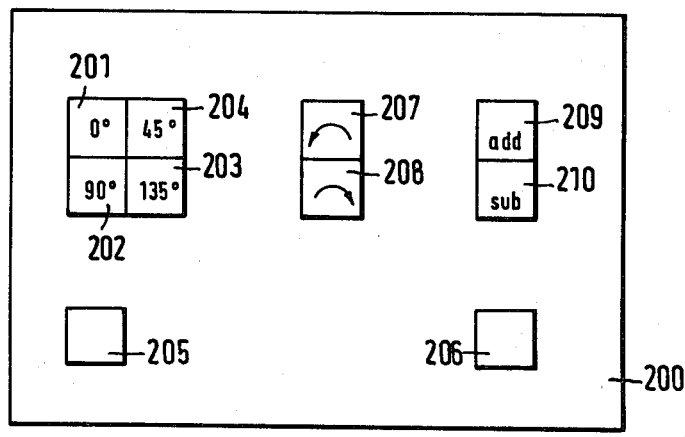
FIG. 2 an embodiment of the operating part for the use in cross cylinder alignment.

In the case of the operating part according to FIG. 2 for using cross cylinder alignment or adjustment, test keys 201, 202, 203 and 204 are provided, which give the control unit 100 the order to adjust the driving mechanisms 12 and 14 so that the lens disc 2 for the spherical test lenses 6 is same-time and rapidly adjusted by one position, corresponding to the example by +0.25 dpt sphere and the lens disc 4 for the cylindrical lenses 2 by two positions, corresponding to −0.50 dpt cylinder and the axial adjustment gear to the angular value associated with the test key 201, 202, 203 or 204. The test keys 201, 202, 203, 204 are in the form of luminous keys and indicate if a cross cylinder formed from the indicated change is additionally connected in the observation optical path 8. A cancel key 205 serves to eliminate the change and thus restore the initial position. However, if the eye under investigation is astigmatic, the visual impression will have been improved in one of the offered positions. In this case, the true dioptric value of the lens combination can be transferred by transmission key 206 into the indicating unit 300 and extinguishes the luminous key which has previously acted.

The approximately-found, angular value of the axis must now be finely adjusted, which is once again brought about with a cross cylinder by adding such a cylinder for the spherocylindrical combination in the phoropter and the visual impressions in its two turning positions are compared with one another. Essentially, the addition of the cross cylinder leads to a rotation of the cylinder axis, this being in the positive rotation direction in one turning position and in the negative rotation direction in the other turning position. If the visual impression is much better in one turning position than in the other, then the cylinder axis must be approximated to the clearer impression. However, if the visual impression is equally poor in both turning positions, the central position forms the true correction axis.

The same result can be obtained if the axis offered to the eye being examined is not adjusted with an additional cross cylinder and instead the axis of the upstream-connected cylindrical lenses is itself adjusted in the positive or negative rotation direction by angular quantities which, mathematically determined, give the same amounts, as a function of the introduced cylinder value, as with a cross cylinder.

Two axial adjustment keys 207 and 208 are provided for this examination, key 207 giving, via control unit 100, the instruction to driving mechanism 15 to vary the axis by a programmed value of, for example, +10° with respect to the random initial position. The other axial adjustment key 208 then brings about an adjustment of the axial position by −20°, so that the axial position is adjusted by ±10°. The axial adjustment keys 207, 208, which are constructed as luminous keys, light up when the axis is pivoted. To restore the initial state, the cancel key 205 is again used or the transmission key 206 makes it possible to transmit to indicating unit 300 the true angular value obtained after pivoting and this, once again, extinguishes the axial adjustment keys 207 or 208. This sets a new central position of the axis and the adjustment can be repeated. However, since such a resetting can only approximate the true axial position in approximate stages, a fine adjustment is programmed. As soon as one of the axial adjustment keys 207, 208 lights up, by again operating this key, the axis can be slowly adjusted in the direction corresponding to the rotation direction marking. The true axial position is found when none of the pivoting positions is preferred by the patient.

For cylinder power adjustment purposes, a cross cylinder is compared in equi-axial manner, either additively or subtractively, with the lenses found. Here, again, the cross cylindrical portion can be represented as a change to the upstream-connected lenses. Here, again, there is an addition key 209 on the one hand, e.g., for +0.25 dpt spherical and −0.50 dpt cylindrical and a subtraction key 210 on the other hand, e.g., for −0.25 dpt spherical and +0.50 dpt cylindrical. These changes are only taken over into the indicating unit 300 if, after a clear improvement to the visual impression, transmission key 206 has been depressed for the purpose of transfer and extinguishing the luminous key. If there has been no improvement to the visual impression, resetting to the initial position can take place with cancel key 205.

Depending on the grading of the test lenses in the lens discs 1, 2, 3, 4, it is possible per program to simulate 100 different cross cylinders in the control unit. In the case of a grading of 0.25 dpt, it is, for example, possible, in addition to the above-mentioned cross cylinder values of ±0.25 dpt, to also form a cross cylinder of ±0.50 dpt. In the program it is then necessary to move on four stages or double the rotation angle during axial adjustment instead of fixing one stage in the spherical value. This is only limited by the time required for adjustment purposes. The change between the settings must be short, so that it is possible to differentiate between two visual impressions.

The invention is not limited to the embodiments described and represented hereinbefore and various modifications can be made thereto without passing beyond the scope of the invention.

What is claimed is:

1. A phoropter for performing subjective refraction tests on the eyes of a patient in accordance with the cross-cylinder method wherein cross-cylinder lenses are customarily employed to carry out said method, comprising:

a set of first lens discs and a number of spherical trial lenses mounted on said first lens discs;

a set of second lens discs and a number of cylindrical trial lenses rotatably mounted on said second lens discs so that the axes of said cylindrical trial lenses can be pivoted about an axis parallel to the axes of said second lens discs;

means for supporting said sets of first and second lens discs for rotation about their respective axes;

first drive means for rotatably driving said sets of first and second lens discs to define an observation optical path extending through selected ones of said spherical trial lenses on said first lens discs and selected ones of said cylindrical trial lenses on said second lens discs;

second drive means for pivoting said cylindrical trial lenses;

control means coupled to said first drive means and to said second drive means for determining the rotational positions to which said spherical and said cylindrical trial lenses are driven about the axes of said first and said second lens discs and for determining the pivot angles to which said cylindrical trial lenses are driven in response to operating input signals, said control means including program means for controlling said first and said second drive means to position certain combinations of said spherical and said cylindrical trial lenses in said observation optical path to establish optically cross-cylinder lens systems in said path;

operating means including instruction entry means coupled to said control means for providing said operating input signals to said control means in response to manual actuation of said selection means to obtain a selected combination of said spherical trial lenses and said cylindrical trial lenses in said observation optical path including said certain combinations for establishing said cross-cylinder lens systems; and indicating means coupled to said control means for displaying specifications for the particular spherical and cylindrical trial lenses positioned in said observation optical path.

2. A phoropter according to claim 1, wherein said first drive means includes a first motor operatively coupled to said sets of first and second lens discs, and a second motor operatively coupled to said cylindrical trial lenses on said second lens discs, and said control means is arranged to actuate said first and said second motors simultaneously.

3. A phoropter according to claim 1, wherein said instruction entry means includes a number of keys corresponding to certain coarse angles wherein said second drive means is controlled so that the axes of the cylindrical trial lenses which are combined with said spherical trial lenses to establish optically said cross-cylinder lens systems can be rotated by said certain coarse angles to determine the existence of astigmatism in the eyes of the patient.

4. A phoropter according to claim 3, wherein said instruction entry means includes a number of keys corresponding to certain fine angles of lesser magnitude than said coarse angles and in both senses of rotation of said cylindrical trial lenses, wherein said second drive means is controlled so that after the axes of the cylindrical trial lenses which are combined with said spherical trial lenses to establish optically said cross-cylinder lens systems are pivoted a selected coarse angle to define a reference angle, the axes of said cylindrical trial lenses can be rotated successively from said reference angle in both senses of rotation by said certain fine angles.

5. A phoropter according to claim 4, wherein said instruction entry means includes a reset key wherein said second drive means is controlled so that the axes of said cylindrical trial lenses are reset to said reference angle.

6. A phoropter according to claim 4, wherein said instruction entry means includes key means for controlling said second drive means so that the axes of said cylindrical trial lenses are finely angularly adjusted in a desired sense of rotation.

7. A phoropter according to claim 1, wherein said spherical trial lenses each have a different dioptric value and sign, and said cylindrical trial lenses each have a different dioptric value and sign, and said program means is arranged to control said first drive means to superimpose successively in said observation optical path one of said spherical trial lenses having a positive dioptric value and one of said cylindrical trial lenses having a negative sign and twice the dioptric value of the superimosed spherical trial lens to establish optically said cross-field lens system in said observation optical path.

8. A phoropter according to claim 7, wherein said instruction entry means includes a cancel key wherein said first drive means is controlled to remove the combined spherical and cylindrical trial lenses which are superimposed in said observation optical path.

9. A phoropter according to claim 7, wherein said program means is arranged to control said first drive means to superimpose in said observation optical path different combinations of said spherical and said cylindrical trial lenses so that cross-field lens systems of different selected powers can be established in said observation optical path.

* * * * *